United States Patent
Shimizu et al.

(10) Patent No.: US 11,284,866 B2
(45) Date of Patent: Mar. 29, 2022

(54) ULTRASONIC SIGNAL PROCESSING DEVICE, ULTRASONIC DIAGNOSIS APPARATUS, AND ULTRASONIC SIGNAL ARITHMETIC PROCESSING METHOD

(71) Applicant: Hitachi, Ltd., Tokyo (JP)

(72) Inventors: Motochika Shimizu, Tokyo (JP); Tomohiko Tanaka, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 142 days.

(21) Appl. No.: 16/637,810

(22) PCT Filed: Sep. 10, 2018

(86) PCT No.: PCT/JP2018/033384
§ 371 (c)(1),
(2) Date: Feb. 10, 2020

(87) PCT Pub. No.: WO2019/163172
PCT Pub. Date: Aug. 29, 2019

(65) Prior Publication Data
US 2020/0397408 A1    Dec. 24, 2020

(30) Foreign Application Priority Data

Feb. 22, 2018   (JP) .............................. JP2018-029558

(51) Int. Cl.
*A61B 8/08*      (2006.01)
*A61B 8/06*      (2006.01)
(Continued)

(52) U.S. Cl.
CPC ............ *A61B 8/5223* (2013.01); *A61B 8/065* (2013.01); *A61B 8/14* (2013.01); *A61B 8/461* (2013.01); *A61B 8/5246* (2013.01); *G01S 15/58* (2013.01)

(58) Field of Classification Search
CPC ......... A61B 8/5223; A61B 8/065; A61B 8/14; A61B 8/461; A61B 8/5246; A61B 8/0883;
(Continued)

(56) References Cited

U.S. PATENT DOCUMENTS 6,381,285 B1    4/2002  Borer
2005/0043622 A1  2/2005  Jensen

FOREIGN PATENT DOCUMENTS

JP          2016-153005 A     8/2016

OTHER PUBLICATIONS

Chi Young Ahn, "Robust Myocardial Motion Tracking for Echocardiography: Variational Framework Integrating Local-to-Global Deformation", Computational and Mathematical Methods in Medicine, 2013, vol. 2013, Article ID 974027, 14 pages.

(Continued)

*Primary Examiner* — Bo Joseph Peng
(74) *Attorney, Agent, or Firm* — Mattingly & Malur, PC

(57) ABSTRACT

Provided are an ultrasonic signal processing device that can evaluate reliability of a velocity vector calculated by sub-pixel tracking, an ultrasonic diagnosis apparatus, and an ultrasonic signal arithmetic processing method. The ultrasonic signal processing device includes an echo signal acquisition unit that acquires an echo signal reflected by an object to be inspected, a velocity vector calculation unit that calculates a velocity vector using the echo signal, a post-parallel-movement signal generation unit that generates a post-parallel-movement signal obtained by approximately parallelly moving the echo signal, an image deformation component extraction unit that extracts an image deformation component which is a change component of a signal value due to deformation of an image from a deviation between the post-parallel-movement signal and the echo (Continued)

signal, and an error energy calculation unit that calculates an error energy of the velocity vector from the image deformation component.

15 Claims, 10 Drawing Sheets

(51) Int. Cl.
    *A61B 8/14*     (2006.01)
    *A61B 8/00*     (2006.01)
    *G01S 15/58*     (2006.01)

(58) Field of Classification Search
    CPC ....... A61B 8/08; G01S 15/58; G01S 7/52071; G01S 7/52073; G01S 15/8984
    See application file for complete search history.

(56) References Cited

OTHER PUBLICATIONS

Masao Shimizu, et al., "Sub-Pixel Estimation Error Cancellation on Area-Based Matching", International Journal of Computer Vision, 2005, 63(3), pp. 207-224.

Toshiyuki Yoshida, "A Reliability Metric for Motion Vectors in Moving Pictures and Its Application", Proceedings D-II of IEICE, May 1997, vol. J80-D-II, No. 5, pp. 1192-1201.

International Search Report of PCT/JP2018/033384 dated Nov. 11, 2018.

[FIG. 1]
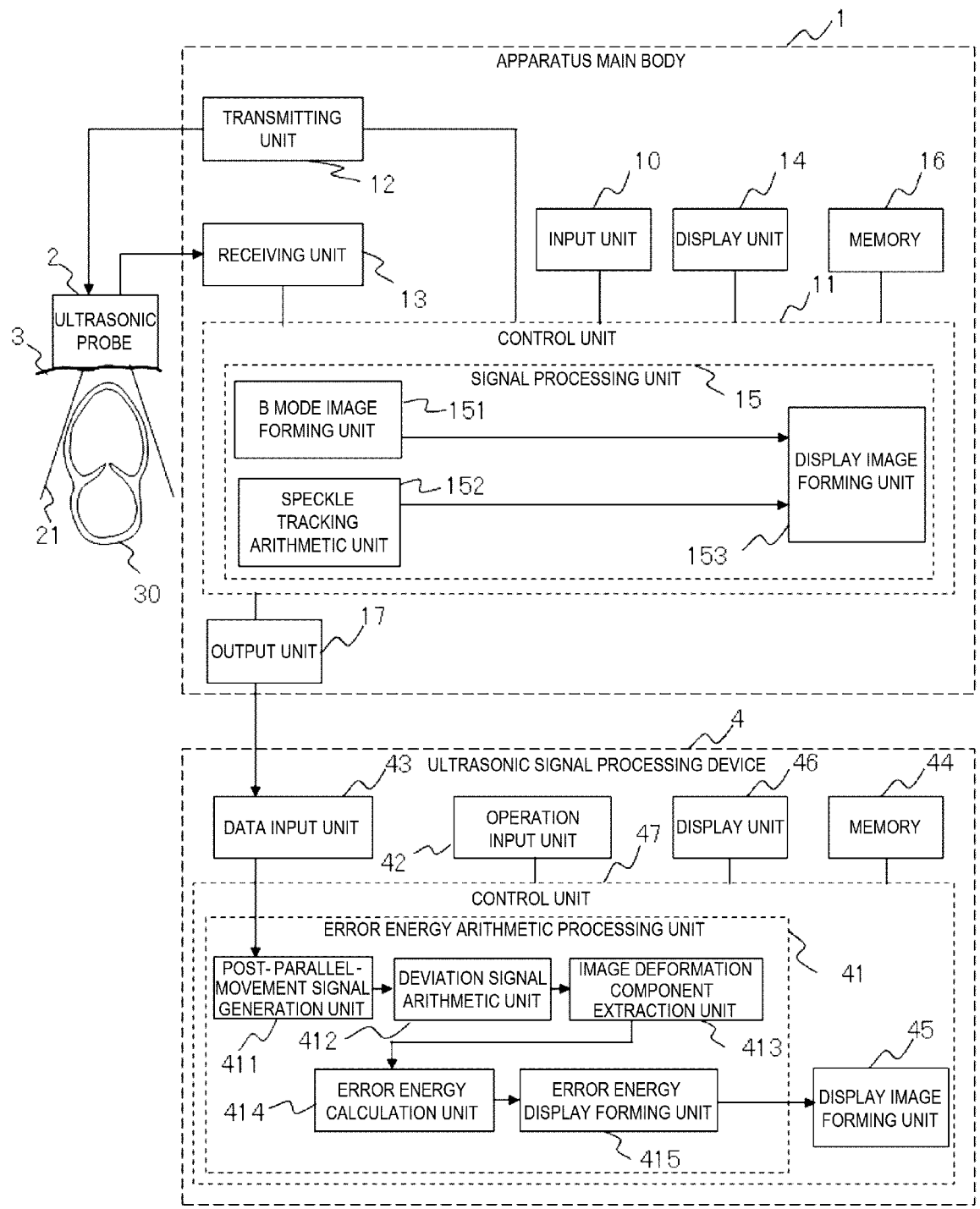

[FIG. 2]
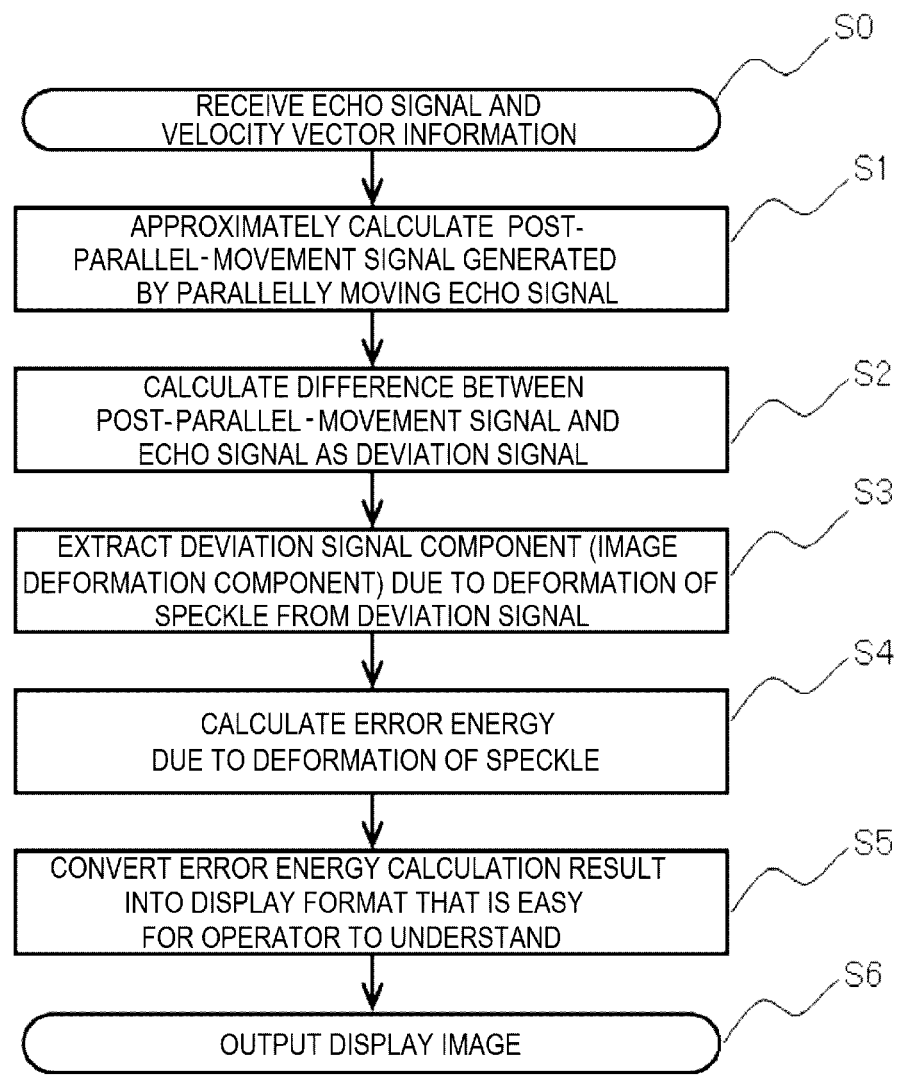

[FIG. 3]
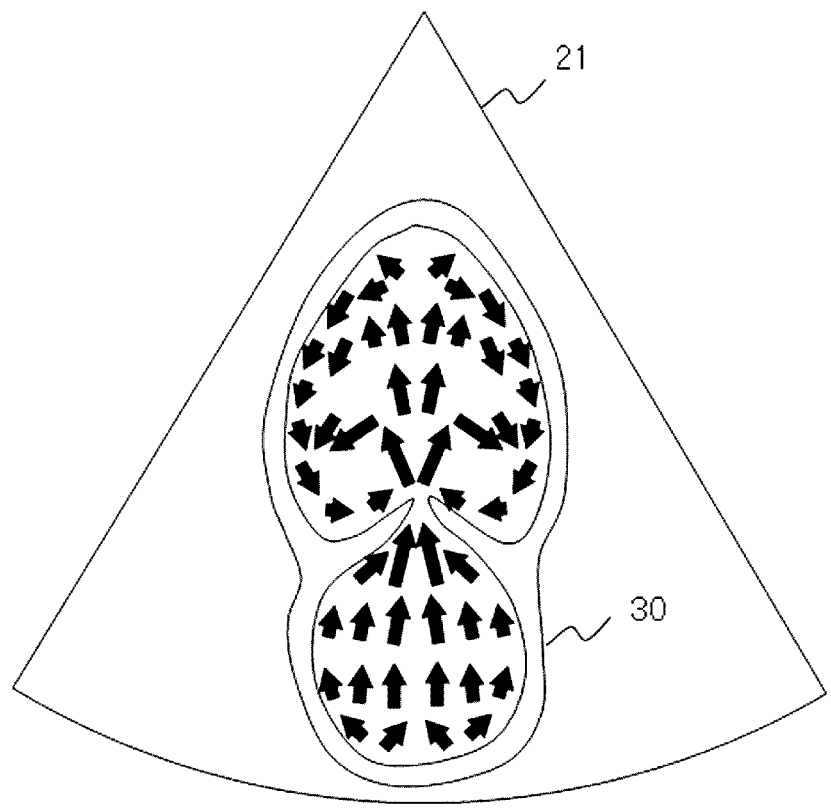
[FIG. 4]
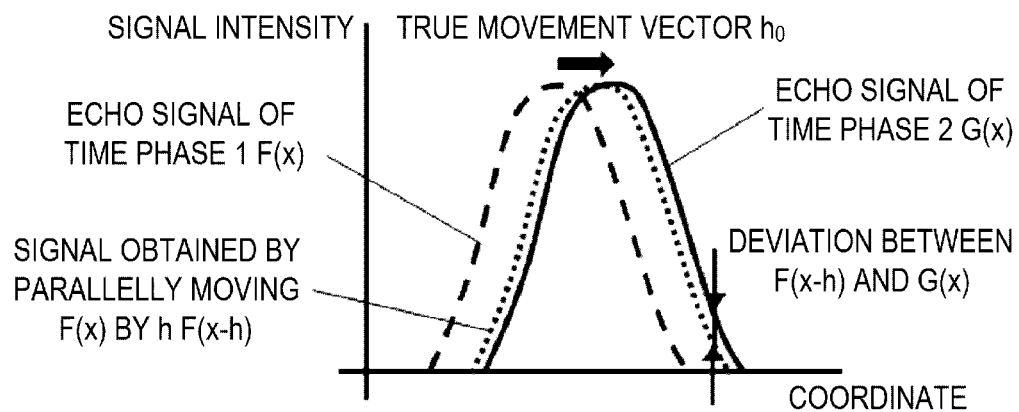

[FIG. 5]
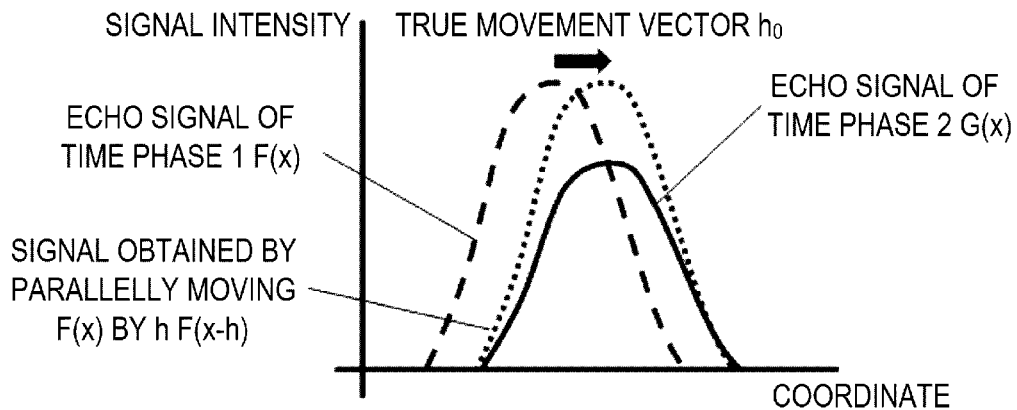
[FIG. 6]
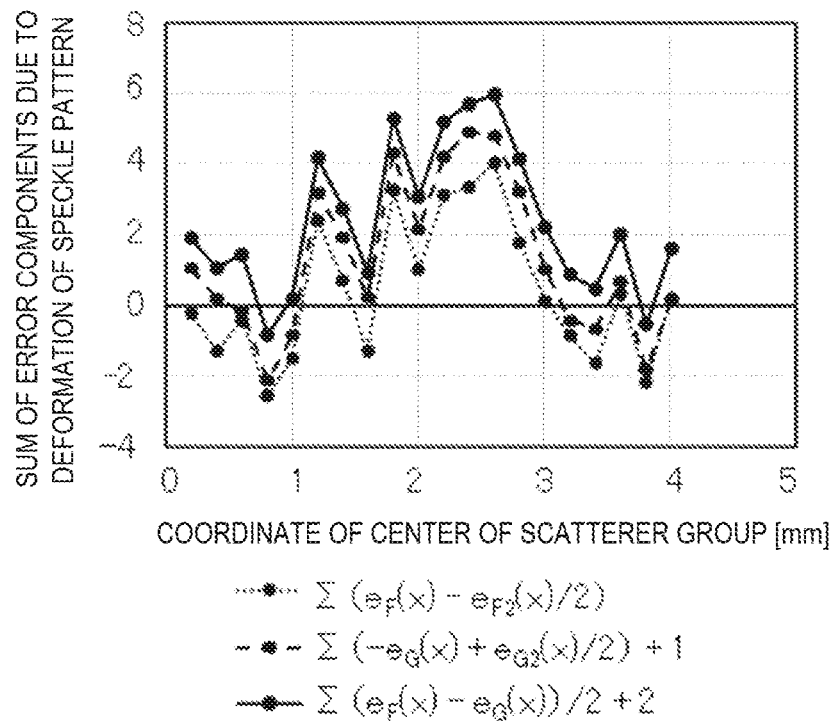

[FIG. 7]
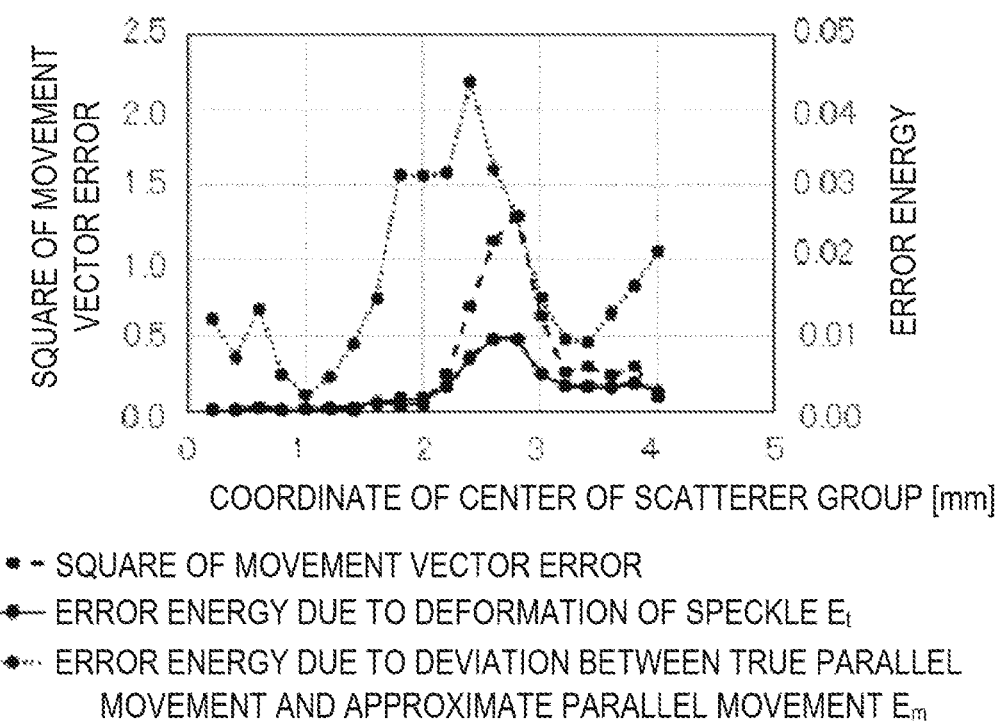
- ■ - SQUARE OF MOVEMENT VECTOR ERROR
—■— ERROR ENERGY DUE TO DEFORMATION OF SPECKLE $E_t$
---■--- ERROR ENERGY DUE TO DEVIATION BETWEEN TRUE PARALLEL MOVEMENT AND APPROXIMATE PARALLEL MOVEMENT $E_m$

[FIG. 8]
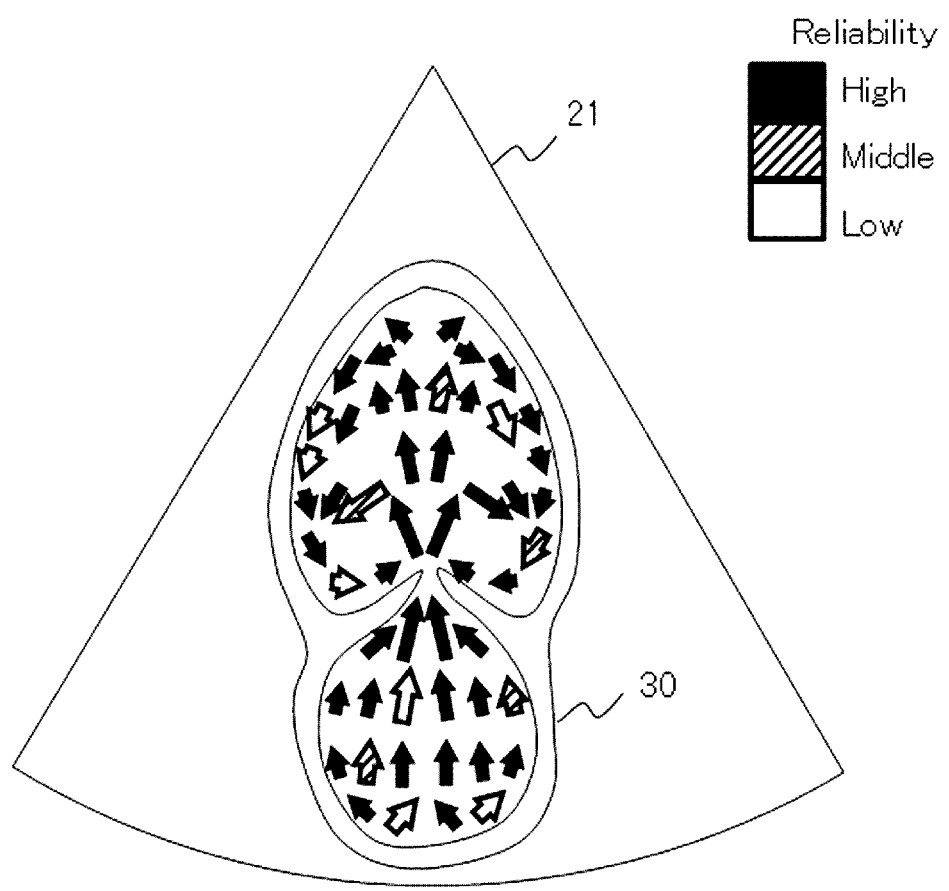

[FIG. 9]
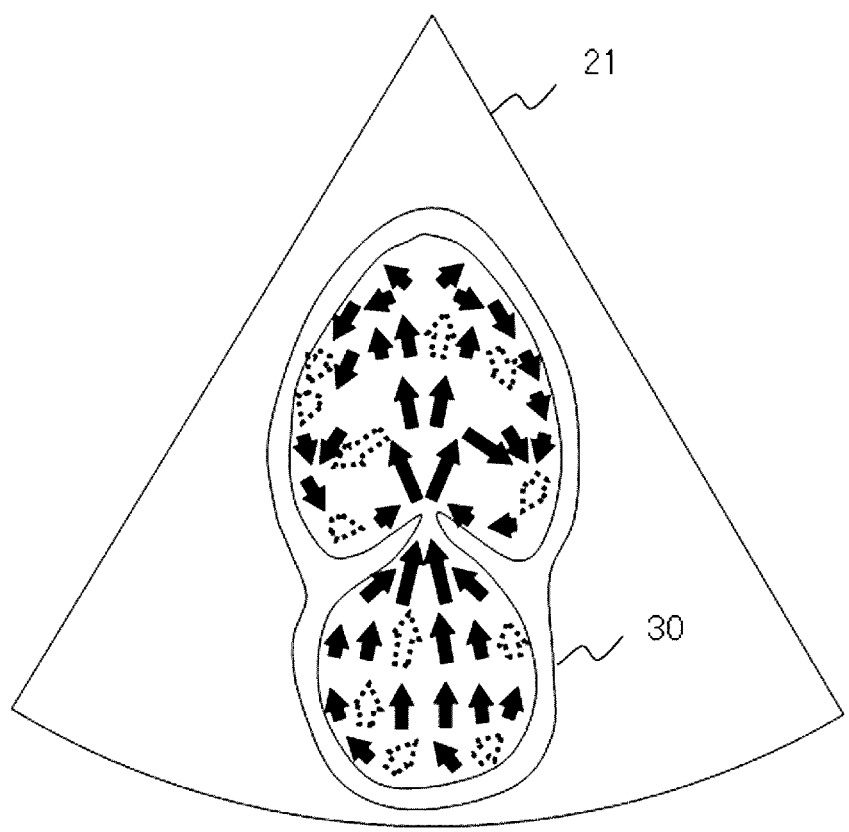

[FIG. 10]
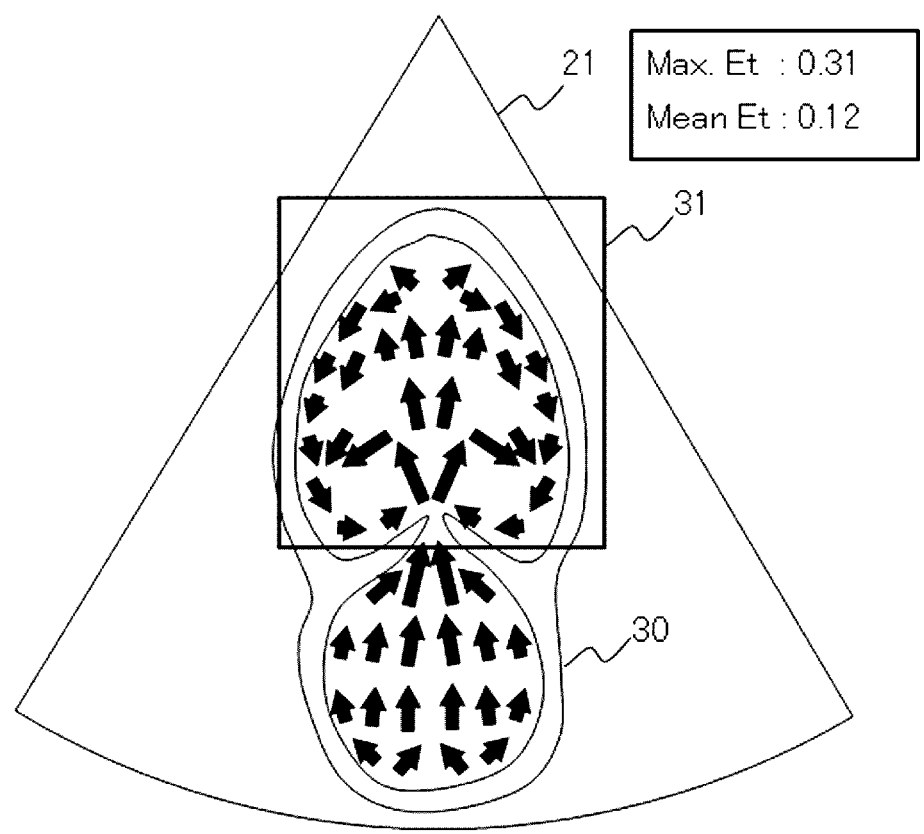

[FIG. 11]
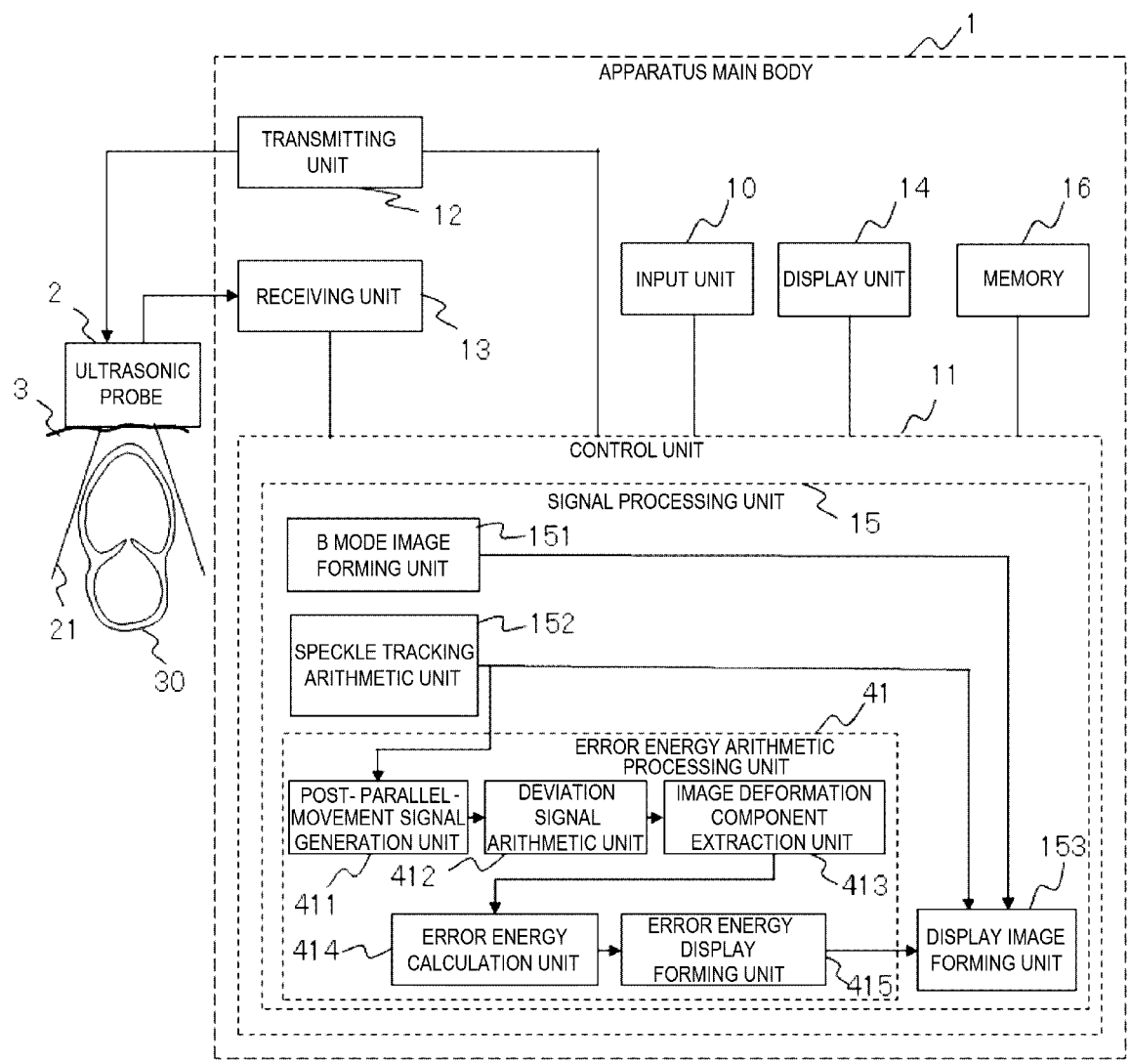

[FIG. 12]
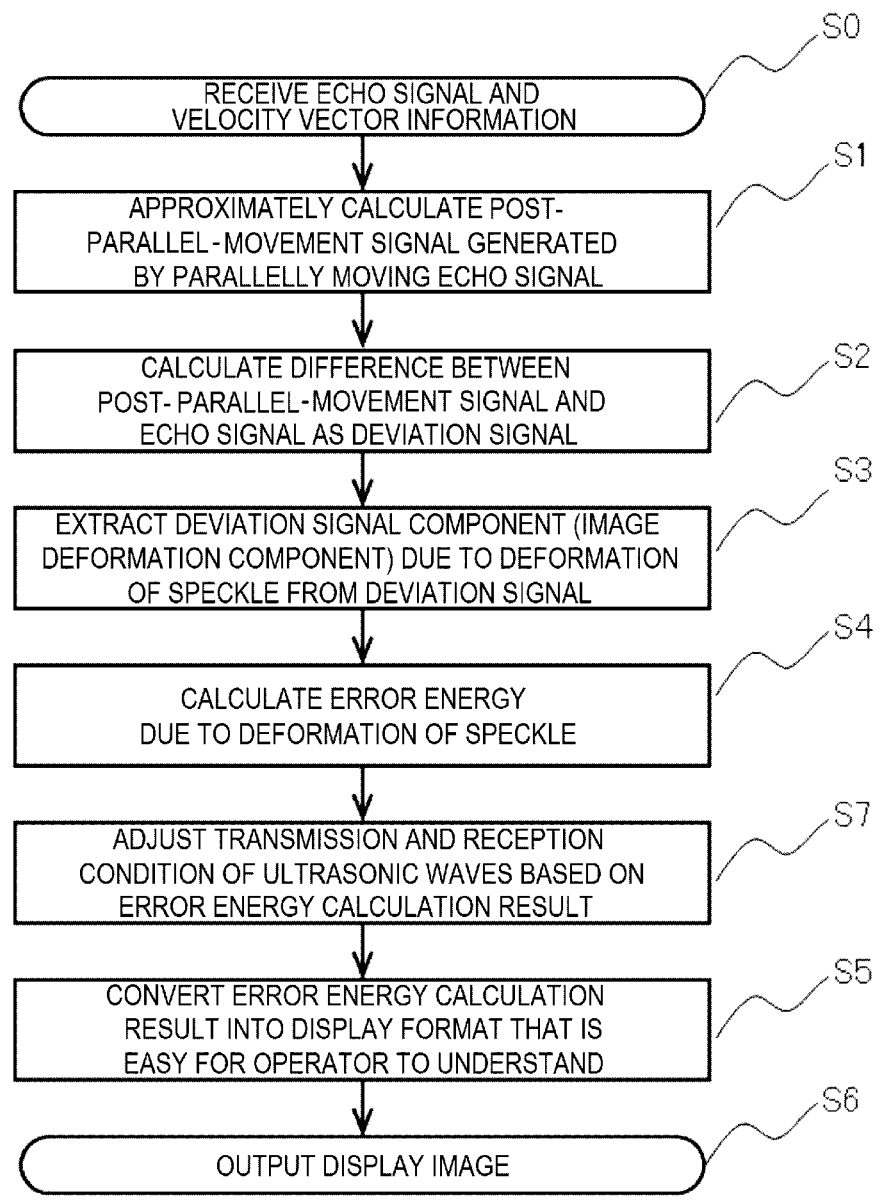

ULTRASONIC SIGNAL PROCESSING DEVICE, ULTRASONIC DIAGNOSIS APPARATUS, AND ULTRASONIC SIGNAL ARITHMETIC PROCESSING METHOD

TECHNICAL FIELD

The present invention relates to a medical ultrasonic signal processing device, and particularly relates to a technique for evaluating reliability of a result obtained by calculating a velocity vector of a motion of a body tissue.

BACKGROUND ART

When determining or making a treatment decision on severity of a cardiovascular disease which is one of main causes of death in developed countries, a motion of a body tissue such as a motion of a myocardium or a blood flow is measured as a velocity vector distribution. A method for measuring the velocity vector distribution by an ultrasonic diagnosis apparatus is a speckle tracking method. The speckle tracking method is a method for tracking speckles which are scattered images of ultrasonic waves reflected by a scatterer in a body tissue between time phases by pattern matching. A velocity vector is calculated from a movement vector and a time interval between time phases. In order to improve a detection resolution of a velocity, sub-pixel tracking is also performed in which the pattern matching is performed in unit of one pixel or less of an ultrasonic image.

It is assumed in the speckle tracking method that a speckle pattern is not deformed before or after a movement. However, the speckle pattern is deformed due to various reasons and makes it difficult to track speckles.

Non-patent Literature 1 discloses that a velocity vector of a myocardium motion is calculated from a speckle pattern that is deformed before and after a movement. Specifically, Non-patent Literature 1 discloses that the velocity vector is calculated even when speckles are greatly moved and deformed by combining an image affine transformation (a geometric transformation) and a Kanade Lucas-Tomasi method (hereinafter, referred to as the KLT method) which is a sub-pixel tracking algorithm.

CITATION LIST

Non-Patent Literature

Non-patent Literature 1: Chi Young Ahn, *Robust Myocardial Motion Tracking for Echocardiography: Variational Framework Integrating Local-to-Global Deformation*, Computational and Mathematical Methods in Medicine, Vol. 2013, Article ID 974027, 14 pages, 2013

SUMMARY OF INVENTION

Technical Problem

Although the velocity vector is calculated by the sub-pixel tracking taking deformation of the speckles into consideration in Non-patent Literature 1, reliability of the calculated velocity vector is not mentioned. Particularly, the velocity vector calculated by the sub-pixel tracking algorithm such as the KLT method includes a component caused by a movement of the speckles and a component caused by the deformation of the speckles. If the two components are not distinguished, it would be difficult to evaluate the reliability of the velocity vector. If the reliability of the velocity vector is not clear, it would be difficult to appropriately determine or make a treatment decision on severity of a cardiovascular disease.

Therefore, an object of the invention is to provide an ultrasonic signal processing device that can evaluate reliability of a velocity vector calculated by sub-pixel tracking, an ultrasonic diagnosis apparatus, and an ultrasonic signal arithmetic processing method.

Solution to Problem

In order to achieve the above object, according to an aspect of the invention, a change component of a signal value due to deformation of an image of speckles or the like is extracted from a deviation signal between an echo signal acquired from an object to be inspected and a post-parallel-movement signal obtained by approximately parallelly moving the echo signal, and an error energy of a velocity vector is calculated from the extracted change component.

Specifically, an ultrasonic signal processing device includes an echo signal acquisition unit that acquires an echo signal reflected by an object to be inspected, a velocity vector calculation unit that calculates a velocity vector using the echo signal, a post-parallel-movement signal generation unit that generates a post-parallel-movement signal obtained by approximately parallelly moving the echo signal, an image deformation component extraction unit that extracts an image deformation component which is a change component of a signal value due to deformation of an image from a deviation signal between the post-parallel-movement signal and the echo signal, and an error energy calculation unit that calculates an error energy of the velocity vector from the image deformation component.

According to a second aspect of the invention, an ultrasonic diagnosis apparatus includes the ultrasonic signal processing device.

According to a third aspect of the invention, an ultrasonic signal arithmetic processing method includes acquiring an echo signal reflected by an object to be inspected, calculating a velocity vector using the echo signal, generating a post-parallel-movement signal obtained by approximately parallelly moving the echo signal, extracting an image deformation component that is a change component of a signal value due to deformation of an image from a deviation signal between the post-parallel-movement signal and the echo signal, and calculating an error energy of the velocity vector from the image deformation component.

Advantageous Effect

According to the invention, an ultrasonic signal processing device that can evaluate reliability of a velocity vector calculated by sub-pixel tracking, an ultrasonic diagnosis apparatus, and an ultrasonic signal arithmetic processing method can be provided.

BRIEF DESCRIPTION OF DRAWINGS

FIG. 1 is a block diagram showing a configuration example of a velocity vector measurement system including an ultrasonic signal processing device according to a first embodiment.

FIG. 2 is a diagram showing an example of a calculation processing flow of an error energy arithmetic processing unit according to the first embodiment.

FIG. 3 is a diagram showing a display example of a velocity vector.

FIG. 4 is a diagram showing a concept of a KLT method.

FIG. 5 is a diagram showing an example in which an error occurs in an arithmetic of velocity vectors due to deformation of a speckle pattern.

FIG. 6 is a diagram showing matching of arithmetic results shown as examples.

FIG. 7 is a diagram showing an example of a square value of a movement vector error and a calculation result of error energies.

FIG. 8 is a diagram showing a display example of error energy for each velocity vector.

FIG. 9 is a diagram showing another display example of error energy for each velocity vector.

FIG. 10 is a diagram showing a display example of a mean value and a maximum value of error energies in a predetermined range.

FIG. 11 is a block diagram showing a configuration example of an ultrasonic diagnosis apparatus having an error energy calculation function according to a second embodiment.

FIG. 12 is a diagram showing an example of a calculation processing flow of a function of adjusting a transmission and/or reception condition of ultrasonic waves based on an error energy calculation result according to the second embodiment.

DESCRIPTION OF EMBODIMENTS

Hereinafter, embodiments of the invention will be described with reference to the drawings.

First Embodiment

FIG. 1 is a block diagram showing a configuration example of a velocity vector measurement system including an ultrasonic signal processing device having an error energy calculation function according to the first embodiment.

An ultrasonic diagnosis apparatus 1 controls an ultrasonic probe 2 and generates an ultrasonic image. The ultrasonic diagnosis apparatus 1 includes an input unit 10, a control unit 11, a transmitting unit 12 that transmits an ultrasonic signal, a receiving unit 13 that receives an echo signal, a display unit 14, a signal processing unit 15, a memory 16, and an output unit 17.

The signal processing unit 15 calculates a velocity vector by a tracking arithmetic based on an echo signal acquired by the ultrasonic diagnosis apparatus 1. That is, the velocity vector is calculated from a time interval between time phases and a movement vector obtained by tracking a part of an image between time phases. Particularly, a speckle tracking arithmetic refers to an arithmetic of tracking, between time phases, speckles that are scattered images of ultrasonic waves reflected by fine structures of cardiomyocytes or red blood cells in blood which are scatterers in a body tissue.

The calculated velocity vector is displayed on the display unit 14 as shown in FIG. 3 or the like. The output unit 17 outputs an echo signal or a processing result of the signal processing unit 15 to the outside. At this time, the echo signal or the processing result of the signal processing unit 15 may be sequentially output, or matters stored in the memory 16 may be collectively output. An ultrasonic signal processing device 4 receives the output of the output unit 17, and calculates, based on the echo signal, an error energy of the velocity vector due to deformation of an image of speckles or the like. Alternatively, the ultrasonic signal processing device 4 may perform the arithmetic of calculating the velocity vector. An arithmetic processing result of the ultrasonic signal processing device 4 may be displayed on a display unit 46 of the ultrasonic signal processing device 4, or may be output to the ultrasonic diagnosis apparatus 1 and displayed on the display unit 14 of the ultrasonic diagnosis apparatus 1.

The ultrasonic probe 2 is brought into contact with a living body 3 of an examinee. A cardiovascular 30 in the living body 3 is irradiated with ultrasonic waves according to a signal generated by the transmitting unit 12. The receiving unit 13 receives an echo signal of the cardiovascular 30 in an imaging range 21. The ultrasonic probe 2 generates continuous waves or pulse waves corresponding to a scanning method, and captures a two-dimensional cross-sectional image or a three-dimensional stereoscopic image.

A function of each component of the ultrasonic diagnosis apparatus 1 will be described. The input unit 10 includes a keyboard or a pointing device for an operator such as a doctor or a technician who operates the ultrasonic diagnosis apparatus 1 to set an operation condition of the ultrasonic diagnosis apparatus 1 in the control unit 11. When information from an external device such as an electrocardiogram is used in an examination, the input unit 10 also has a function of acquiring information from the external device.

The control unit 11 controls the transmitting unit 12, the receiving unit 13, the display unit 14, and the signal processing unit 15 based on the operation condition of the ultrasonic diagnosis apparatus 1 set by the input unit 10. The control unit 11 can be constructed in, for example, a central processing unit (CPU) of a computer system.

The transmitting unit 12 includes an oscillator that generates a signal having a predetermined frequency, and sends a drive signal to the ultrasonic probe 2. Although not shown, the receiving unit 13 includes an analog to digital (A/D) converter having a receiving circuit and a general sampling frequency from 10 MHz to 50 MHz. In addition, the receiving unit 13 performs signal processing such as phasing addition, detection, and amplification on an echo signal received by the ultrasonic probe 2. Alternatively, the A/D converter may be provided in a preceding stage of the signal processing unit 15 instead of being provided in the receiving unit 13. In this case, the signal processing unit 15 performs the signal processing such as phasing addition, detection, and amplification. Although not shown, the receiving unit 13 may include a received data memory that temporarily stores an echo signal of each receiving element of the ultrasonic probe 2 or of each opening that binds elements.

The signal processing unit 15 includes a B mode image forming unit 151 and a display image forming unit 153. The B mode image forming unit 151 forms an ultrasonic image such as a tomographic image which is referred to as a B mode image and calculates various pieces of processing data used for an ultrasonic diagnosis by, for example, software executed by the CPU. The signal processing unit 15 may further include a speckle tracking arithmetic unit 152 that calculates a velocity vector according to a speckle tracking arithmetic. The display image forming unit 153 forms an image to be presented to the operator based on a processing result of the B mode image forming unit 151 or the speckle tracking arithmetic unit 152. A part of or all functions of components of the signal processing unit 15 may be implemented by software executed by the same CPU that constitutes the control unit 11 or by different CPUs, or may be implemented by hardware such as an application specific integrated circuit (ASIC), a field-programmable gate array (FPGA), and a graphics processing unit (GPU).

The memory 16 stores an echo signal, and information necessary for an arithmetic in the signal processing unit 15 such as information instructed by the operator via the input unit 10 and a processing result of the signal processing unit 15 including a B mode image, a display image of a velocity vector distribution, and the like. In addition, the memory 16 may store an arithmetic processing result of the ultrasonic signal processing device 4 such as an error energy.

The output unit 17 outputs an echo signal or a processing result of the signal processing unit 15 to the outside. An output mode may be a mode in which the echo signal or the processing result of the signal processing unit 15 is directly transmitted to the ultrasonic signal processing device 4 via a cable or the like, or may be a mode in which the echo signal or the processing result of the signal processing unit 15 is written and transferred to an external storage medium such as a portable hard disk or a USB memory.

The ultrasonic signal processing device 4 receives output information from the ultrasonic diagnosis apparatus 1, and calculates an error energy of a velocity vector due to deformation of an image of speckles or the like based on an echo signal. An error energy arithmetic processing unit 41 performs arithmetic processing of calculating an error energy. The error energy arithmetic processing unit 41 includes, as main elements, a post-parallel-movement signal generation unit 411, a deviation signal arithmetic unit 412, an image deformation component extraction unit 413, an error energy calculation unit 414, and an error energy display forming unit 415.

The post-parallel-movement signal generation unit 411 generates a post-parallel-movement signal obtained by approximately parallelly moving an echo signal. The deviation signal arithmetic unit 412 calculates a deviation signal between the post-parallel-movement signal and the echo signal. The image deformation component extraction unit 413 extracts, from the deviation signal, an image deformation component which is a change component of a signal value due to the deformation of an image of speckles or the like. The error energy calculation unit 414 calculates an error energy from the image deformation component. The error energy display forming unit 415 converts the calculated error energy into a display format that is easy for the operator to understand. Details of each unit will be described below.

The error energy arithmetic processing unit 41 includes the above elements as a program. The program is read and executed by a CPU to implement a function to be described below. Alternatively, the program may be executed by other hardware such as an ASIC, an FPGA, and a GPU.

The ultrasonic signal processing device 4 includes an operation input unit 42, a data input unit 43, a memory 44, a display image forming unit 45, the display unit 46, and a control unit 47. The operation input unit 42 is a keyboard, a pointing device, or the like that receives an operation from the operator. The data input unit 43 receives an output from the ultrasonic diagnosis apparatus 1. The memory 44 stores received data or an arithmetic processing result. The display image forming unit 45 forms an image to be presented to the operator based on an arithmetic processing result or an output result from the ultrasonic diagnosis apparatus 1. However, the ultrasonic signal processing device 4 is not necessarily a dedicated device and may be a computer that executes processing in cooperation with a program decompressed on a memory and hardware such as a CPU.

The main elements of the error energy arithmetic processing unit 41 will be described in detail.

The post-parallel-movement signal generation unit 411 approximately calculates, from an echo signal acquired by the ultrasonic diagnosis apparatus 1, a post-parallel-movement signal which is an echo signal generated by parallelly moving the echo signal acquired by the ultrasonic diagnosis apparatus 1 at a predetermined velocity for a predetermined time. The predetermined time is, for example, a time between time phases of two signals that are compared by the pattern matching of the speckle tracking arithmetic. The predetermined velocity is, for example, a velocity vector obtained by the speckle tracking arithmetic. Further, the most basic method for an approximate parallel movement arithmetic is an approximate expression of a parallel movement assumed in the speckle tracking arithmetic. For example, the approximate parallel movement arithmetic is a first linear approximation when the KLT method is used. A high speed arithmetic can be performed by using the first linear approximation. Alternatively, other methods may be applied to the approximate parallel movement arithmetic. For example, the approximate parallel movement arithmetic may be performed by fitting a signal that is discretely acquired with a continuous function and analytically calculating a function obtained by parallelly moving a fitting function. Arithmetic accuracy can be improved by fitting the signal with the continuous function.

The deviation signal arithmetic unit 412 calculates, as a deviation signal, a change in an echo signal generated by the approximate parallel movement by comparing the post-parallel-movement signal and the echo signal acquired by the ultrasonic diagnosis apparatus 1. Combinations of signals to be compared may be determined according to a calculation processing flow to be described below.

The image deformation component extraction unit 413 extracts, from the deviation signal, an image deformation component that is a change component of a signal value due to the deformation of an image of speckles or the like using the deviation signal, the post-parallel-movement signal, the echo signal, or the like. At this time, combinations of signals to be used may be determined according to the calculation processing flow to be described below.

The error energy calculation unit 414 calculates an error energy of a velocity vector due to the deformation of an image of speckles or the like using the image deformation component, the deviation signal, the post-parallel-movement signal, the echo signal, or the like.

The error energy display forming unit 415 converts a calculation result of the error energy into a display format that is easy for the operator to understand. A possible format will be described in the calculation processing flow to be described below.

An example of operation of the error energy arithmetic processing unit 41 will be described with reference to the calculation processing flow shown in FIG. 2 based on the configuration of the apparatus described above.

Step S1

After the post-parallel-movement signal generation unit 411 receives the output information of the ultrasonic diagnosis apparatus 1 from the data input unit 43, the post-parallel-movement signal generation unit 411 approximately calculates a post-parallel-movement signal obtained by parallelly moving an echo signal of a predetermined time phase at a predetermined velocity for a predetermined time. Formula 1 is an expression for generating a signal after an echo signal F(x) is parallelly moved by h according to a first linear approximation in an example in which the KLT method is used in the speckle tracking arithmetic. A comma on a right shoulder represents a spatial derivative. For simplicity, a one-dimensional spatial coordinate system is described in the following description. However, the same arithmetic is performed on a signal of a two-dimensional spatial coordinate system or a three-dimensional spatial coordinate system in an actual arithmetic. h represents a movement vector.

$$F_{+h}(x)=F(x)-h\,F'(x) \quad \text{[Formula 1]}$$

As shown in FIG. 4, the KLT method is an arithmetic method for calculating the movement vector h so as to obtain a smallest deviation signal between an echo signal G(x) of a predetermined time phase 2 and a signal F(x−h) obtained by approximately parallelly moving the echo signal F(x) of a predetermined time phase 1 by h. At this time, an approximate parallel movement of F(x) is assumed by Formula 1 and the deviation signal between F(x−h) and G(x) is defined as energy E(h) by Formula 2.

$$E(h)=\Sigma_x[\{F(x)-hF'(x)\}-G(x)]^2 \quad \text{[Formula 2]}$$

When the movement vector h is equal to a true movement vector $h_0$, the energy E (h) of the deviation signal has a minimum value and a spatial derivative of E(h) is equal to 0. That is, Formula 3 is established.

$$\frac{dE}{dh}\bigg|_{h_0} = \sum_x 2 - [-F'(x)\{F(x)-G(x)\}+h_0 F'(x)^2] = 0 \quad \text{[Formula 3]}$$

Formula 4 is obtained by transforming Formula 3.

$$h_0 = \frac{\sum_x F'(x)[F(x)-G(x)]}{\sum_x F'(x)^2} \quad \text{[Formula 4]}$$

In an arithmetic using the KLT method, a velocity vector is calculated using Formula 4. It is assumed as a premise that the echo signal F(x) is parallelly moved. The velocity vector may be calculated using Formula 5 obtained from an energy of a deviation signal between F(x) and a signal G(x+h) obtained by approximately parallelly moving G(x) by −h.

$$h_0 = \frac{\sum_x G'(x)[F(x)-G(x)]}{\sum_x G'(x)^2} \quad \text{[Formula 5]}$$

It is assumed in Formula 5 that the echo signal G(x) is obtained by parallelly moving the signal G(x+h). Alternatively, Formula 6 may be used to balance influences of signals F(x) and G(x) that are signals before and after an image of speckles or the like is moved.

$$h_0 = \frac{\sum_x \left[\frac{F'(x)+G'(x)}{2}\right][F(x)-G(x)]}{\sum_x \left[\frac{F'(x)+G'(x)}{2}\right]^2} \quad \text{[Formula 6]}$$

According to Formula 6, an influence of random noises contained in a signal can be reduced. Hereinafter, an example of using the most basic Formula 4 will be described.

In ultrasonic imaging, a speckle pattern is deformed before and after a movement due to a variation of sound pressure and an artifact in a transmission beam, electrical noises in signal transmission, and the like, and a signal is deformed. Here, the variation of sound pressure in a transmission beam will be described as a factor having great influence. The variation of sound pressure in a transmitted beam gives a different sound pressure for each coordinate. Therefore, sound pressures received by scatterers change before and after a movement, and an intensity of ultrasonic scattering of the scatterers also changes. As a result, even when all of the scatterers are moved similarly, a speckle pattern is deformed as shown in FIG. 5 and an error due to the deformation of the speckle pattern occurs in an arithmetic result of Formula 4. Since Formula 4 is based on the parallel movement approximated by Formula 1, the parallel movement deviates from a premise of a true parallel movement and an error due to the deviation also occurs in the arithmetic result of Formula 4.

Therefore, a change of a signal value before and after a movement is obtained by adding, to a change of a signal value merely caused by a movement of speckles, an error due to the deformation of a speckle pattern and an error due to the deviation between the true parallel movement and an approximated parallel movement. The error due to the deformation of the speckle pattern is to be extracted at this time. In order to separate the error due to the deformation of the speckle pattern from the error due to the deviation between the true parallel movement and the approximated parallel movement and extract the error due to the deformation of the speckle pattern in the processing to be described below, the post-parallel-movement signal generation unit 411 calculates one or a plurality of post-parallel-movement signals. For example, post-parallel-movement signals shown in Formula 1, Formula 7, formula 8, and Formula 9 are calculated. However, it is not necessary to calculate all of the post-parallel-movement signals. A signal used by the deviation signal arithmetic unit 412 or the image deformation component extraction unit 413 to be described below may be calculated.

$$G_{-h}(x)=G(x)+hG'(x) \quad \text{[Formula 7]}$$

$$F_{\pm h}(x)=F_{+h}(x)+hF'_{+h}(x)=F(x)-h^2 F''(x) \quad \text{[Formula 8]}$$

$$G_{\pm h}(x)=G_{-h}(x)-hG'_{-h}(x)=G(x)-h^2 G''(x) \quad \text{[Formula 9]}$$

The post-parallel-movement signal shown in Formula 7 is obtained by calculating a signal obtained by parallelly moving the echo signal G(x) of the predetermined time phase 2 by −h in a backward time manner for a predetermined time. The post-parallel-movement signal shown in Formula 8 is obtained by calculating a signal obtained by parallelly moving the echo signal F(x) of the predetermined time phase 1 by h and then parallelly moving the echo signal F(x) of the predetermined time phase 1 by −h. The post-parallel-movement signal shown in Formula 9 is obtained by calculating a signal obtained by parallelly moving the echo signal G(x) of the predetermined time phase 2 by −h and then parallelly moving the echo signal G(x) of the predetermined time phase 2 by h. A signal obtained by moving an echo signal twice in opposite directions should be exactly the same as an original signal if a parallel movement is correctly performed. However, the signal is actually different from the original signal since an approximate parallel movement is performed.

Step S2

After the post-parallel-movement signal is received from the post-parallel-movement signal generation unit 411, the deviation signal arithmetic unit 412 calculates a difference between the post-parallel-movement signal and the echo signal as a deviation signal. Examples of the calculated deviation signal are shown in Formula 10, Formula 11, Formula 12, and Formula 13. However, it is not necessary to calculate all deviation signals. A signal used by the image deformation component extraction unit 413 to be described later may be calculated.

$$e_F(x) = F_{+h}(x) - G(x) = F(x) - hF'(x) - G(x) \quad \text{[Formula 10]}$$

$$e_G(x) = G_{-h}(x) - F(x) = G(x) + hG'(x) - F(x) \quad \text{[Formula 11]}$$

$$e_{F2}(x) = F_{\pm h}(x) - F(x) = -h^2 F''(x) \quad \text{[Formula 12]}$$

$$e_{G2}(x) = G_{\pm h}(x) - G(x) = -h^2 G''(x) \quad \text{[Formula 13]}$$

A deviation signal $e_F(x)$ shown in Formula 10 is a deviation between a signal obtained by parallelly moving the echo signal F(x) of the predetermined time phase 1 to the predetermined time phase 2 in a forward time manner and an actual signal G(x) of the predetermined time phase 2. A deviation signal $e_G(x)$ shown in Formula 11 is a deviation between a signal obtained by parallelly moving the echo signal G(x) of the predetermined time phase 2 to the predetermined time phase 1 in a backward time manner and an actual signal F(x) of the predetermined time phase 1. A deviation signal $e_{F2}(x)$ shown in Formula 12 is a deviation between an original signal F(x) and a signal obtained by repeating a parallel movement of the echo signal F(x) of the predetermined time phase 1 by predetermined movement vectors h and −h. A deviation signal $e_{G2}(x)$ shown in Formula 13 is a deviation between an original signal G(x) and a signal obtained by repeating a parallel movement of the echo signal G(x) of the predetermined time phase 2 by the predetermined movement vectors h and −h.

Step S3

After the deviation signal is received from the deviation signal calculation unit 412, the image deformation component extraction unit 413 extracts, from the deviation signal, an image deformation component that is a change component of a signal value due to the deformation of an image of speckles or the like using a deviation signal, a post-parallel-movement signal, an echo signal, or the like. Within the deviation signal, as shown in Formula 10 or Formula 11, a deviation between a signal that is moved in different coordinates and an echo signal of a time phase that is different from an original signal includes an image deformation component that is an error due to the deformation of a speckle pattern and a deviation error component that is an error due to a deviation between a true parallel movement and an approximated parallel movement. At this time, although the deviation error component is constant regardless of a direction of a movement vector, positive and negative image deformation components are reversed by reversing the direction of the movement vector. A deviation between an original signal and a signal obtained by repeating an approximate parallel movement of the signal only includes a deviation error component for twice as shown in Formula 12 or Formula 13. Therefore, a deviation error component can be removed from a deviation signal to extract an image deformation component $e_t$, for example, by arithmetics shown in Formula 14, Formula 15, and Formula 16.

$$e_t(x) = e_F(x) - \frac{e_{F2}(x)}{2} \quad \text{[Formula 14]}$$

$$e_t(x) = -e_G(x) + \frac{e_{G2}(x)}{2} \quad \text{[Formula 15]}$$

$$e_t(x) = \frac{e_F(x) - e_G(x)}{2} \quad \text{[Formula 16]}$$

Arithmetic results of Formula 14, Formula 15, and Formula 16 as shown in FIG. 6 are matched to confirm that the image deformation component $e_t$ can be extracted by Formula 16 which is an arithmetic obtained by combining Formula 10 and Formula 11. However, FIG. 6 shows a result of forming with an ultrasonic simulator a speckle pattern created by a scatterer group that moves gradually from a center of a transmission beam and adding image deformation components $e_t$ calculated by Formula 14, Formula 15, and Formula 16 in a pixel group that is the same with the velocity vector arithmetic. Since three graphs have highly matched arithmetic results and can not be discriminated, a shift +1 is given to a result of Formula 15 and a shift +2 is given to a result of Formula 16 in FIG. 6.

Formula 14 is used to calculate a velocity vector assuming a parallel movement of the signal F(x) and extract an image deformation component when Formula 4 is used in the KTL arithmetic. The Formula 15 is used to calculate a velocity vector assuming a parallel movement of the signal G(x) and extract an image deformation component when Formula 5 is used in the KTL arithmetic. The Formula 16 is used to calculate a velocity vector in which influences of both F(x) and G(x) are balanced and extract an image deformation component when Formula 6 is used in the KLT arithmetic. Therefore, an image deformation component may be extracted by selecting any one of the Formula 14 to Formula 16 depending on what the operator emphasizes. For example, when a real-time property is emphasized, it is preferable to use an arithmetic mode in which only one parallel movement of F(x) or G(x) is assumed, that is, Formula 14 or Formula 15. When calculation accuracy of a velocity vector is emphasized, it is preferable to use an arithmetic mode in which the influences of both F(x) and G(x) are balanced, that is, Formula 16. Specifically, the operator may select whether to emphasize the real-time property or the calculation accuracy on an operation screen and determine which one of Formula 14 to Formula 16 will be used according to an selection of the operator.

Step S4

After the image deformation component is received from the image deformation component extraction unit 413, the error energy calculation unit 414 calculates an error energy due to deformation of an image of speckles or the like using an image deformation component, a deviation signal, a post-parallel-movement signal, an echo signal, or the like. At this time, an influence of an unexpected abnormal signal component that occurs locally can be reduced to obtain a stable calculation value using an addition value obtained by adding components obtained on a pixel basis in a predetermined range. A definition of the error energy may use an image deformation component as it is, or an absolute value of the image deformation component. Processing such as squaring which is handled as power and logarithmically converting an absolute value or a square value to change a scale may be performed. Since slight deformation of speckles is a main error factor in a weak original signal, the slight deformation may be standardized by an intensity of echo signals. For example, a value obtained by squaring an image deformation component $e_t$ as power is added in a pixel group that is the same with the velocity vector arithmetic, and is further normalized by a value obtained by squaring the echo signal F(x) to define an error energy $E_t$ as shown in Formula 17.

$$E_t = \frac{\sum_x [e_t(x)]^2}{\sum_x [F(x)]^2} \qquad \text{[Formula 17]}$$

FIG. 7 shows a change in the error energy $E_t$ due to deformation of speckles based on the definition in Formula 17 when the speckle pattern created by the scatterer group is formed by the ultrasonic simulator and a center of the scatterer group is gradually moved from the center of the transmission beam. FIG. 7 also shows a value obtained by calculating a square of a movement vector error (a norm of a difference from a true movement vector and value of setting a 100% error as 1), and an error energy $E_m$ caused by a deviation between a true parallel movement and an approximated parallel movement. The error energy $E_m$ is defined by Formula 18.

$$E_m = \frac{\sum_x \left[\frac{e_F(x) + e_G(x)}{2}\right]^2}{\sum_x [F(x)]^2} \qquad \text{[Formula 18]}$$

The error energy $E_t$ due to the deformation of an image of speckles or the like changes following the square of the movement vector error. On the other hand, the error energy $E_m$ caused by the deviation between the true parallel movement and the approximated parallel movement varies independent of the square of the movement vector error. The error energy $E_m$ caused by the deviation between the true parallel movement and the approximated parallel movement is several times larger than the error energy $E_t$ caused by deformation of speckles. An error energy correlated with the movement vector error would not be obtained if the error energy $E_m$ is not excluded.

Step S5

After the error energy calculation result is received from the error energy calculation unit 414, the error energy display forming unit 415 converts the error energy calculation result into a display format that is easy for the operator to understand. For example, as shown in FIG. 8, a two-dimensional spatial distribution of velocity vectors may be displayed on a B-mode image in a superimposed manner, a length of an arrow that represents a velocity vector may correspond to an absolute value of the velocity vector, and a color or a shade of an arrow may correspond to a value of an error energy. That is, a velocity vector having high reliability may be highlighted with a dark color. In addition, a threshold may be provided for an error energy. As shown in FIG. 9, a velocity vector whose error energy is larger than the threshold, that is, a velocity vector having low reliability may not be displayed. According to display formats shown in FIG. 8 or FIG. 9, reliability of calculated velocity vectors can be presented to the operator. As shown in FIG. 10, a statistical value such as an average value or a maximum value of error energies of a velocity vector group in a range of interest 31 specified by the operator or in the entire imaging range 21 may be shown. According to a display format in FIG. 10, reliability of the velocity vector group in a displayed frame image can be presented to the operator. A frame image that satisfies a requirement that, for example, the statistical value of the error energies of the velocity vector group in a predetermined range such as the range of interest 31 is larger than the threshold, may be automatically excluded or extracted to be displayed.

Second Embodiment

FIG. 11 is a block diagram showing a configuration example in a case where the ultrasonic signal processing device 4 according to the first embodiment is assembled in the ultrasonic diagnosis apparatus 1.

A function and a configuration of the ultrasonic diagnosis apparatus 1 are the same as those in the first embodiment. In addition, the signal processing unit 15 includes the error energy arithmetic processing unit 41. Similar to the first embodiment, the error energy arithmetic processing unit 41 includes the post-parallel-movement signal generation unit 411, the deviation signal arithmetic unit 412, the image deformation component extraction unit 413, the error energy calculation unit 414, and the error energy display forming unit 415. The signal processing unit 15 includes the above-described elements as a program. The program is read and executed by a CPU to implement a function. However, a CPU responsible for a part or all functions of the error energy arithmetic processing unit 41 may be different from a CPU responsible for a basic function of the signal processing unit 15.

Since a velocity vector can be calculated while performing ultrasonic imaging near an examinee by assembling the ultrasonic signal processing device 4 in the ultrasonic diagnosis apparatus 1, an error energy calculation result can be confirmed in real time. Compared to a case where the ultrasonic signal processing device 4 and the ultrasonic diagnosis apparatus 1 are provided separately, the second embodiment has an advantage in terms of data communication between devices. Since there is a restriction on usage of wireless communication between devices in order to avoid an operation failure of an electronic machine relating to life support in a medical field, data communication between devices is performed using wired connection such as a cable or an external storage medium such as a portable hard disk and a USB memory. Data communication between devices is unnecessary by assembling the ultrasonic signal processing device 4 in the ultrasonic diagnosis apparatus 1, and mobility of the ultrasonic diagnosis apparatus 1 can be utilized.

An operation in the case where the signal processing unit 15 also functions as the error energy arithmetic processing unit 41 according to the embodiment is basically the same as a calculation processing flow of the error energy arithmetic processing unit 41 according to the first embodiment. Since the ultrasonic signal processing device 4 is provided in the ultrasonic diagnosis apparatus 1, an operation of the ultrasonic diagnosis apparatus 1 can be controlled based on an error energy calculation result. FIG. 12 shows a calculation processing flow of the ultrasonic diagnosis apparatus 1 that automatically adjusts a transmission and/or reception condition of ultrasonic waves based on the error energy calculation result.

Step S1 to Step S4 are the same as those in the calculation processing flow according to the first embodiment. The present embodiment is different from the first embodiment in Step S7 that is performed after Step S4. However, step S7 may be performed simultaneously with step S5, or may be performed after step S5.

Step S7

After an error energy calculation result is received from the error energy calculation unit 414, the control unit 11 adjusts a transmission and/or reception condition of ultrasonic waves based on the error energy calculation result. Here, the transmission and/or reception condition of ultrasonic waves indicates a convergence and/or diffusion state of a transmission beam, a sound pressure distribution, a pulse repetition frequency, the number of reception regions or reception beams that are used for calculation of velocity vectors, a transmission and reception sequence, and the like. These transmission and/or reception conditions are factors that affect measurement accuracy of a velocity vector by speckle tracking.

An example of a method for adjusting the transmission and/or reception condition of ultrasonic waves will be described. First, several combinations of transmission and/or reception conditions to be tested are prepared in advance. Next, error energies of individual velocity vectors and a statistical value, for example, an average value or a maximum value, of error energies of a velocity vector group in a predetermined range are calculated for the prepared combinations. Then, a combination of transmission and/or reception conditions is determined based on a calculation result. At this time, a combination satisfying a predetermined condition such as a minimum average value of error energies in a predetermined range may be selected from the combinations prepared in advance, or a combination may be newly constructed by performing a multiple regression analysis or the like based on a test result.

Another example of the method for adjusting the transmission and/or reception condition of ultrasonic waves includes a method for dynamically searching for a combination of transmission conditions satisfying a predetermined condition by calculating error energies of individual velocity vectors and a statistical value of error energies while changing the transmission and/or reception conditions. For example, a combination of transmission conditions having a minimum average value of error energies of a velocity vector group in a predetermined range is dynamically searched while the transmission and/or reception conditions are changed. At this time, in order to efficiently search for a combination, how to change a searching direction such as a parameter may be determined based on knowledge of an influence on a measurement error or an error energy of a velocity vector from the transmission and/or reception conditions that are specified in advance.

REFERENCE SIGN LIST 1 ultrasonic diagnosis apparatus
10 input unit
11 control unit
12 transmitting unit
13 receiving unit
14 display unit
15 signal processing unit
151 B-mode image forming unit
152 speckle tracking arithmetic unit
153 display image forming unit
16 memory
17 output unit
2 ultrasonic probe
21 imaging range
3 living body
30 cardiovascular
31 range of interest
4 ultrasonic signal processing device
41 error energy arithmetic processing unit
411 post-parallel-movement signal generation unit
412 deviation signal arithmetic unit
413 image deformation component extraction unit
414 error energy calculation unit
415 error energy display forming unit
42 operation input unit
43 data input unit
44 memory
45 display image forming unit
46 display unit
47 control unit

The invention claimed is:

1. An ultrasonic signal processing device comprising:
an ultrasonic probe that receives an echo signal reflected by body tissue;
a receiver, coupled to the ultrasonic probe, including a receiving circuit and an analog to digital converter that receives the echo signal received by the ultrasonic probe;
a first computer coupled to the receiver, the first computer programmed to calculate a velocity vector of motion of the tissue using the echo signal from a time interval between time phases and a movement vector obtained by tracking speckles between time phases, the speckles are scattered images of ultrasonic waves reflected by structures of the body tissue;
a second computer coupled to the first computer, the second computer programmed to:
generate a post-parallel-movement signal by parallelly moving the echo signal at a predetermined velocity for a predetermined time,
extract an image deformation component which is a change component of a signal value due to deformation of an image from a deviation signal between the post-parallel-movement signal and the echo signal, and
calculate an error energy of the velocity vector from the image deformation component.

2. The ultrasonic signal processing device according to claim 1,
wherein the second computer is further programmed to extract the image deformation component by removing, from the deviation signal, a deviation error component which is an error caused by a deviation between a true parallel movement and an approximate parallel movement.

3. The ultrasonic signal processing device according to claim 2,
wherein the second computer is further programmed to remove the deviation error component using:
a deviation signal between a parallel movement signal obtained by approximately parallelly moving an echo signal of a first time phase to a second time phase and an echo signal of the second time phase, and
a deviation signal between a parallel movement signal obtained by repeating an approximate parallel movement of the echo signal of the first time phase and the echo signal of the first time phase.

4. The ultrasonic signal processing device according to claim 2,
wherein the second computer is further programmed to remove the deviation error component using:
a deviation signal between a parallel movement signal obtained by approximately parallelly moving an echo signal of a first time phase to a second time phase and an echo signal of the second time phase, and
a deviation signal between a parallel movement signal obtained by approximately parallelly moving the echo signal of the second time phase to the first time phase and the echo signal of the first time phase.

5. The ultrasonic signal processing device according to claim 1,
wherein the second computer is further programmed to set a display format of the error energy.

6. The ultrasonic signal processing device according to claim 5,
wherein the second computer is further programmed to set a color or a shade of an arrow that represents the velocity vector according to a value of the error energy.

7. The ultrasonic signal processing device according to claim 5,
wherein the second computer is further programmed to set a display format including a statistical value of error energies of a group of velocity vectors in an entire imaging range or in a predetermined range.

8. The ultrasonic signal processing device according to claim 5,
wherein the second computer is further programmed to set whether to display a frame image according to whether a statistical value of error energies of a group of velocity vectors in an entire imaging range or in predetermined range satisfies a predetermined requirement.

9. The ultrasonic signal processing device according to claim 1,
wherein the second computer is further programmed to calculate the error energy using an addition value obtained by adding an absolute value or a square value of the image deformation component in a predetermined range.

10. The ultrasonic signal processing device according to claim 9,
wherein the second computer is further programmed to calculate the error energy by normalizing the addition value by the echo signal.

11. The ultrasonic signal processing device according to claim 1,
wherein the second computer is further programmed to calculate the post-parallel-movement signal by a first linear approximation using a spatial differential value of the echo signal.

12. The ultrasonic signal processing device according to claim 1,
wherein the second computer is further programmed to calculate the post-parallel-movement signal by analytically calculating a function obtained by parallelly moving a continuous function fitted to the echo signal.

13. An ultrasonic diagnosis apparatus comprising:
the ultrasonic signal processing device according to claim 1.

14. The ultrasonic diagnosis apparatus according to claim 13,
wherein the first computer is further programmed to adjust a transmission and/or reception condition of an ultrasonic wave based on the error energy or a statistical value of the error energy,
the transmission and/or reception condition of the ultrasonic wave indicates a convergence and/or diffusion state of a transmission beam, a sound pressure distribution, a pulse repetition frequency, a number of reception regions or reception beams that are used for calculation of velocity vectors, or a transmission and reception sequence.

15. An ultrasonic signal arithmetic processing method comprising:
acquiring an echo signal reflected by body tissue;
calculating a velocity vector of motion of the tissue using the echo signal from a time interval between time phases and a movement vector obtained by tracking speckles between time phases, the speckles are scattered images of ultrasonic waves reflected by structures of the body tissue;
generating a post-parallel-movement signal obtained by parallelly moving the echo signal at a predetermined velocity for a predetermined time;
extracting an image deformation component which is a change component of a signal value due to deformation of an image from a deviation between the post-parallel-movement signal and the echo signal; and
calculating an error energy of the velocity vector from the image deformation component.

\* \* \* \* \*